United States Patent [19]

Wing

[11] Patent Number: 4,781,288
[45] Date of Patent: Nov. 1, 1988

[54] HERMETICALLY SEALED FLAT CASE

[76] Inventor: George S. Wing, 531 Esplanade, Apt. 515, Redondo Beach, Calif. 90277

[21] Appl. No.: 107,684

[22] Filed: Oct. 13, 1987

[51] Int. Cl.[4] ............................................. A45D 33/00
[52] U.S. Cl. ........................................ 206/37; 206/69; 220/4 B; 132/293
[58] Field of Search ................ 220/4 B; 206/37, 69, 206/235; 132/83 R

[56] References Cited

U.S. PATENT DOCUMENTS 4,289,232  9/1981  Seibel et al. .......................... 206/37
4,569,438  2/1986  Sheffler ................................ 206/37

Primary Examiner—George T. Hall
Attorney, Agent, or Firm—Plante, Strauss & Vanderburgh

[57] ABSTRACT

There is disclosed a very compact flat case for carrying prophylactics, such as condoms and the like. The overall dimensions of the case are approximately the same as a large coin. The case has flat top and bottom members which are hinged together with concentric cylindrical walls which support a resilient seal such as an O-ring. One or both of the mating walls are inclined to insure that sealing pressure is applied to the O-ring. The case has a closure which has a pair of detent balls, one each of each of the top and bottom members. The detent balls seat in mating recesses in the opposite member.

4 Claims, 2 Drawing Sheets

HERMETICALLY SEALED FLAT CASE

BACKGROUND OF THE INVENTION

1. Field of Invention

This invention relates to a hermetically sealed case and, in particular, to a carrying case for prophylactics.

2. Brief Statement of the Prior Art

Prophylactic devices such as condoms and the like are commonly packaged in sealed foil wrappers which are torn open to gain access. This necessary frangibility also renders the wrapper easily subject to puncture and its contents to damage. Additionally, the foil wrappers are imprinted with conspicuous material.

Various flat cases have been suggested for prophylactic devices, e.g., see U.S. Pat. No. 4,289,232 which discloses a case suitable for containing a diaphragm and prophylactic cream or jelly. U.S. Pat. No. 1,726,143 discloses a box for the inconspicuous packaging of condoms and other prophylactic devices, but without any suitable means for hermetically sealing the container. U.S. Pat. No. 2,006,212 discloses a flat flexible package which is formed of metal foil.

None of the prior packages provides the convenience and cleanliness of contents which are desirable or necessary for a prophylactic container. Specifically, the container should have a positive closure with a closure which will maintain the case in a closed and sealed state to prevent circulation of air and deterioration of the material of the prophylactic device. Additionally, the case should also seal against liquids to prevent any loss of liquids such as spermicides or germicides that can be added to its contents. The case, while providing a safe secure seal, must also have a reliable and convenient latch. Preferably, the case should have an attractive external appearance. For this purpose, the case must be an essentially thin, flat case of minimal thickness and an adequate cross sectional area for containing the prophylactic device.

BRIEF DESCRIPTION OF THE INVENTION

The invention is a very compact case for carrying prophylactics, such as condoms. The case has flat top and bottom members which are hinged together with concentric cylindrical walls which support a resilient seal such as an O-ring. One or both of the mating walls are inclined to insure that sealing pressure is applied to the O-ring. The case has a closure which has a pair of detent balls, one each of each of the top and bottom members. The detent balls seat in mating recesses in the opposite member.

The invention serves the purpose of offering a safe alternative to the foil wrapped prophylactics by permitting the user to open the foil wrapped package under the most suitable conditions and remove the prophylactic from its wrapper and inspect it for damage or manufacturing flaws. The prophylactic can then be placed in the case of the invention, applying germicides or other material, if desired. Since the case is entirely rigid, it insures against damage, such as puncturing, of its contents. The principal purpose of the inventions to encourage and assist in the prevention of acquiring or transmitting the deadly aids virus.

BRIEF DESCRIPTION OF THE DRAWINGS

The invention will be described with reference to the FIGURES of which.

DESCRIPTION OF PREFERRED EMBODIMENT

Figure 1:
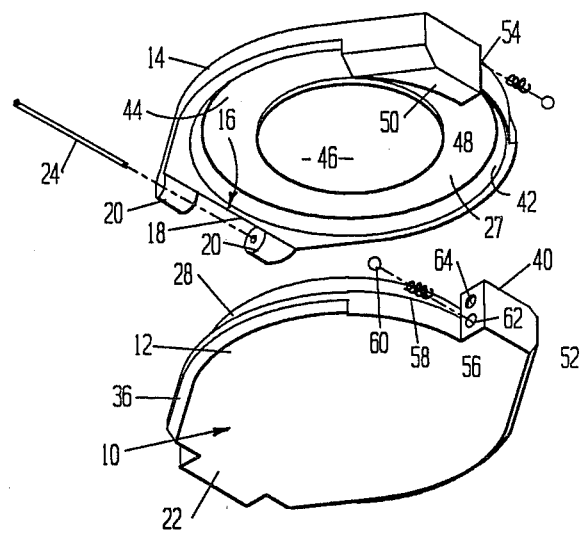
FIG. 1 is an exploded perspective view of the case of the invention.

Referring now to FIG. 1, the case 10 of the invention is shown as comprising a bottom member 12 and a cover member 14 which are hinged together with hinge means 16 located at one side or end 18 of the assembly. The hinge means 16 comprises a pair of hinge blocks 20 which are integral with the cover member 14 and which are laterally spaced apart a sufficient distance to receive between their opposing faces the hinge block 22 of the bottom member 12. The hinge blocks 20 and 22 have continuous through bores which are aligned to receive a hinge pin 24 that can be permanently secured in the assembly by press fitting or other suitable means of attachment.

The bottom member 12 has a central cavity which is entirely surrounded by a circular, upright wall 28. Extending entirely about he outside of the upright wall 28 is a flat ledge (not shown in FIG. 1), and the hinge block 22, previously identified, is integral with this ledge. The bottom edge 36 of the bottom member 12 can be chamfered, preferably at a 45° angle, as illustrated. An annular groove entirely surrounds the outside of the upright wall 28, and this groove serves as a seat for a resilient seal 40, which is prefeably an O-ring.

The cover member 14 has a central cylindrical recess 27 which has a sufficient diameter to be snugly received about the upright wall 28 of the bottom member 12. Preferably the inside wall 42 of this recess is inclined at an angle from 10° to 45° to provide the desirable sealing action, as described hereinafter. The inside bottom surface 44 of the cover member 14 can have a raised, centrally located cylindrical boss 46, and a similar boss (not shown) can be provided on the inside bottom surface of the bottom member.

On its end 48, which is opposite its hinge end 18, the cover member 14 has a closure abutment block 50. A coacting abutment block 52 is provided on the bottom member 12. These abutment blocks extend towards and terminate short of the midline of the case, thereby providing opposing, coacting closure surfaces 54 and 56.

A pair of detents, each comprising a resilient, compression spring 58 and a detent ball 60 are mounted in lateral bores such as 62 are provided in each of the abutment blocks 50 and 52. These detents are aligned in a vertically stacked array. Each abutment block has a receptacle or recess 64 on its abutment face for receiving the detent ball of the opposite abutment block.

Figure 2:
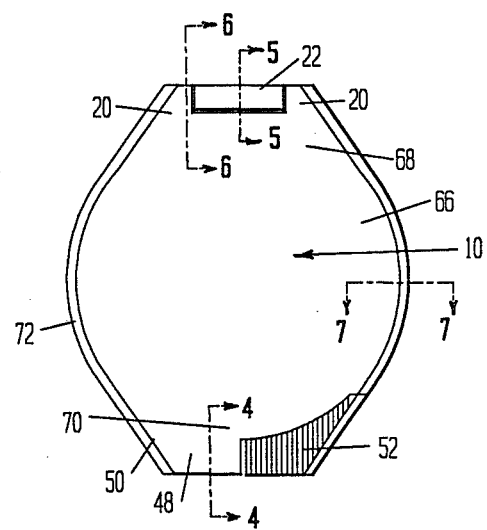
FIG. 2 is a top view of the case.
Figure 3:
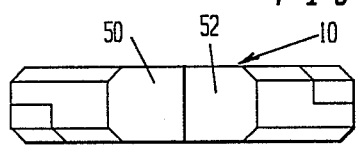
FIG. 3 is an end view of the case.

Referring now to FIGS. 2 and 3, the case of the invention is shown in its closed configuration. FIG. 2 is a view of the top of the case and the case, which has a central, arcuate body 66 having opposite trapezoidal wings 68 and 70. These wings form the hinge blocks 20 and 22, and the closure abutments 50 and 52, previously described. As illustrated, the hing blocks and closure abutment block of the cover are coplanar with the top surface of the central body. The cover, as the bottom, has a beveled edge 72 also illustrated in FIG. 3 that extends entirely about the periphery of the cover except for the rear edges 74 of the hinge blocks 20.

FIG. 3 is a view from the closure end 48 of the case 10 and illustrates the closure abutment blocks 50 and 52, which are each integral with their respective cover and bottom members.

Figure 4:
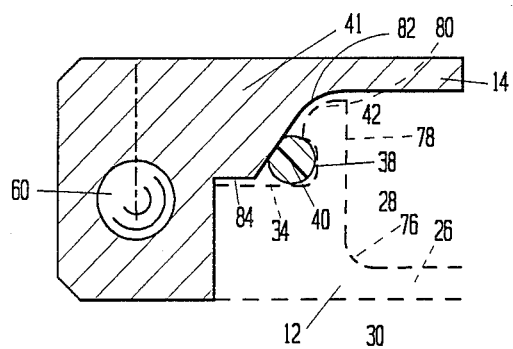
FIG. 4 is a view along lines 4-4' of FIG. 2.

Referring now to FIG. 4, there is shown a cross sectional view through the closure blocks, along line 4–4' of FIG. 2. As there illustrated, the cover member 14 is shown in solid lines and the bottom member 12 is shown in phantom lines, in a closed position. The bottom member 12 has a central cavity 26 entirely surrounded with an upright cylindrical wall 28. Preferably the inside corner 76 between the bottom surface 30 and inside wall 78 is filleted with a smooth radius of curvature for ease in maintaining cleanliness of the case. The upper edge 80 of the cylindrical wall 28 is beveled or can be arcuately contoured, as illustrated. A flat ledge 34 entirely surrounds the outside of the upright wall 28 approximately at the middle of the case. An annular groove 38 is formed in the outside of the upright cylindrical wall 28 and an resilient seal 40, preferably an O-ring is seated in this groove.

The cover member 14 has a central recess 27 with an upstanding cylindrical wall 41 which has an inclined inside wall 42. Preferably, the inside wall 42 is inclined at an angle of from 10° to about 45°. The corner 82 between the inside wall 42 and the undersurface 44 of the cover member 14 is also preferably filleted as illustrated with a smooth curvature, again for cleanliness. This curvature can generally conform to the curvature of the arcuate upper edge 72 of the upright cylindrical wall 28 of the bottom member 12. The cover member 14 also has an annular flat ledge 84 which, when the members are closed, abuts with the flat ledge 34 of the bottom member 12. In the closed position, as illustrated in FIG. 4, the wall 42 of the cover member 14 resiliently bears against the resilient seal 40, deflecting and compressing the seal member to secure a gas and liquid tight engagement between the bottom and cover members.

The cover member 14 is securely retained in sealed relationship to the bottom member 12 by the latch mechanism. As previously mentions, the latch mechanism includes a plurality of detents, preferably a pair of detent balls 60 that are resilient biased into mating recesses 64. The location of the centers of the detents are shown by the center lines of FIG. 4. The detent which is positioned in the closure abutment block 50 of the cover member 14 is also illustrated in its position.

Figure 5:
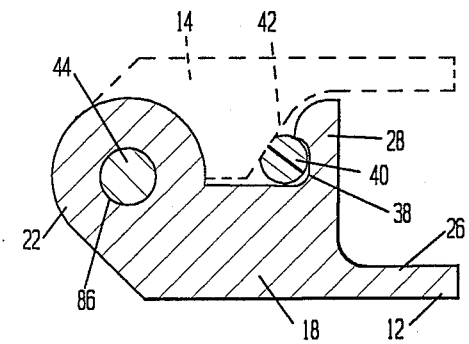
FIG. 5 is a view along lines 5-5' of FIG. 2.
Figure 6:
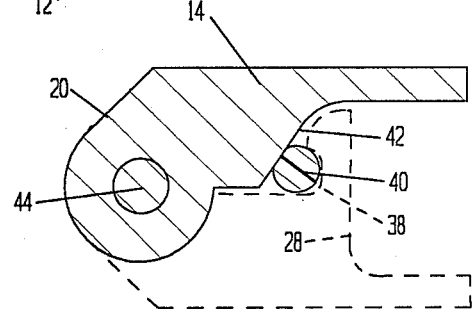
FIG. 6 is a view along lines 6-6' of FIG. 2.

Referring now to FIGS. 5 and 6, there are illustrated sectional views through the hinge end 18 of the case 10. As there illustrated, the bottom member 12 has a centrally positioned single hinge block 22 which has a generally arcuate cross section and is integrally formed on the hinge end 18 of the bottom member 12. The block 22 has a single centrally positioned through aperture 86 which receives the hinge pin 44. This aperture is in alignment with a similar aperture in the two hinge blocks 20 of the cover member 14. The upright wall 28 of the bottom member 12 has the same shape and size throughout its length about the central cavity 26 of the bottom member 12, and has the annular groove 38 that receives the resilient O-ring which is deflected and compressed by the inclined sidewall 42 of the upper member 14, all as illustrated in FIG. 5.

Figure 7:
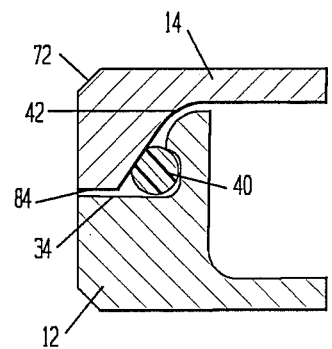
FIG. 7 is a view along lines 7—7' of FIG. 2.

Referring now to FIG. 7, there is illustrated a sectional view through the side of the case 10, along lines 7–7' of FIG. 2. As there illustrated, the cover member 14 has a vertical outer wall with a beveled outside edge 72. The cover member 14 has a flat inside peripheral ledge 84 which abuts with the flat ledge 34 that extends about the periphery of the bottom member 12. As illustrated in FIG. 7, the resilient O-ring seal 40 is also illustrated in its compressed configuration, sealed against the inclined inside wall 42 of the cover member 14.

Figure 8:
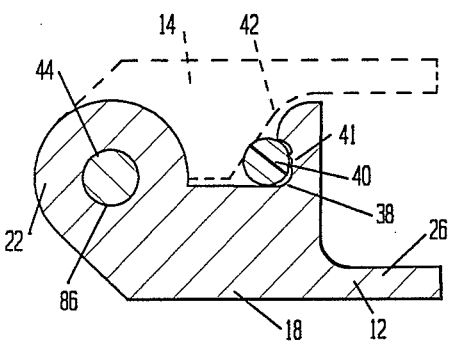
FIG. 8 is a sectional view similar to FIG. 5, but of an alternative embodiment.

Referring now to FIG. 8, there is illustrated a sectional view through the bottom member 12 at the hinge end 18 of the case 10. This illustration is substantially the same as that of FIG. 5, except that the annular groove 38 has a plurality of grooves, forming ribs 41 along the entire length of the annular groove 38 to improve the seal which it forms with the resilient O-ring 40. As before, the O-ring is deflected and compressed by the inclined sidewall 42 of the upper member 14 and seats against the ribs 41.

The case 10 of the invention is very inconspicuous and is of a suitable size for carrying in a pocket or purse. The overall dimensions of the case are only slightly larger than a large coin, e.g., a silver dollar. Since the seal extends about the periphery or circumference of coaxial inner bottom wall and outer wall of the cover member, the sealing surfaces are substantially vertical rather than horizontal. Consequently, it is not necessary to machine planar surfaces for precise fitting. Instead, the precisely machined surfaces are cylindrical and their machining can be readily accomplished. Additionally, the mating and sealing surfaces of the members are inclined thereby ensuring a sealed configuration without necessity for close precision or tolerances in the fabrication of the case. The use of two detents achieves adequate locking pressure without excessive wear which would otherwise occur when using a single detent. The result is a very compact and attractive case which has a positive lock or seal that will maintain security of its contents.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. A sealed case for flat objects which comprises:
   a. a flat bottom having an upright circular wall with an inclined top edge, and a peripheral flat ledge with an annular groove extending about the exterior of said wall, above said ledge;
   b. a flat cover having a recessed central well with an inside diameter to closely conform about said upright circular wall when said cover is closed on said bottom, said recess being surrounded by a peripheral edge with an inside wall inclined at an angle from 10 to 45 degrees;
   c. hinge means comprising first and second hinge blocks on one end of said bottom and cover, respectively, with aligned through apertures and receiving a hinge pin for hinged interconnection of said bottom and cover at said one end thereof;
   d. closure means comprising first and second closure abutments opposing each other on each of said bottom and cover at their ends opposite said one end, a plurality of ball detents and cooperating receptacles for said ball detents located in stacked array on said closure means; and e. resilient seal means carried in said annular groove for compressive contact with the inclined inner wall of the recessed central well of said cover.

2. The sealed case of claim 1 wherein said hinge means includes a pair of hinge blocks laterally spaced apart on said cover and receiving a single hinge block of said bottom therebetween.

3. The sealed case of claim 1 wherein said closure abutments are integral extensions of their respective bottom and cover and meet along the midline of said case.

4. The sealed case of claim 3 wherein said each of said closure abutments has one detent ball received in a mounting bore with resilient means biasing it outwardly from said bore.

* * * * *